(12) United States Patent
Corbett

(10) Patent No.: US 6,375,034 B1
(45) Date of Patent: Apr. 23, 2002

(54) GLOVE DISPENSER

(76) Inventor: Adrian Corbett, 11791 Scripps Cape Vista Pointe, San Diego, CA (US) 92131

( * ) Notice: Subject to any disclaimer, the term of this patent is extended or adjusted under 35 U.S.C. 154(b) by 0 days.

(21) Appl. No.: 09/669,494

(22) Filed: Sep. 25, 2000

Related U.S. Application Data

(63) Continuation of application No. 09/531,395, filed on Mar. 21, 2000.

(51) Int. Cl.[7] .................................................. B65H 1/00
(52) U.S. Cl. .............................. 221/46; 221/45; 221/32; 221/30; 221/38
(58) Field of Search ............................ 221/30, 32, 45, 221/38, 25, 46, 191; 2/161.7; 223/111

(56) References Cited

U.S. PATENT DOCUMENTS

| | | | |
|---|---|---|---|
| 4,844,293 A | * 7/1989 | McLaughlin | 221/34 |
| 4,915,272 A | * 4/1990 | Vlock | 223/111 |
| 4,951,815 A | * 8/1990 | Ulbrich | 206/213 |
| 5,020,160 A | * 6/1991 | Cano | 2/159 |
| 5,175,977 A | * 1/1993 | Crawford et al. | 53/399 |
| 5,456,354 A | * 10/1995 | Wood | 206/278 |
| 5,584,390 A | * 12/1996 | Wood | 206/233 |
| 5,816,440 A | * 10/1998 | Shields et al. | 221/45 |
| 5,921,434 A | * 7/1999 | Hollander et al. | 221/34 |
| 6,021,919 A | * 2/2000 | Kelly | 221/25 |
| 6,053,380 A | * 4/2000 | Sherrod | 223/111 |
| 6,095,326 A | * 8/2000 | Madhat et al. | 206/233 |

FOREIGN PATENT DOCUMENTS

FR 2621902 A * 4/1989 ........... B65H/35/06

* cited by examiner

*Primary Examiner*—Christopher P. Ellis
*Assistant Examiner*—Michael E Butler
(74) *Attorney, Agent, or Firm*—Steins & Associates, P.C.

(57) ABSTRACT

An Improved Glove Dispenser is disclosed. Also disclosed is a device that permits a user to don gloves without first touching their exterior. The disclosed device includes a plurality of gloves attached by their cuffs to a filament, with the filament and cuffs being dispensed from an exchangeable glove cartridge. It is a further feature that the dispenser may be responsive to a user's voice. Furthermore, the invention provides a new method for donning gloves that will prevent user contamination of the gloves by touching the exterior of the gloves during the donning process.

17 Claims, 5 Drawing Sheets

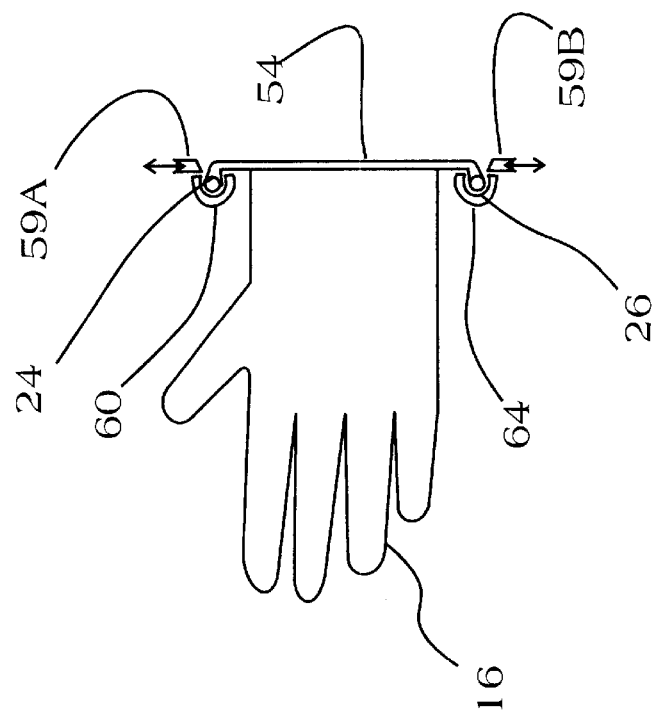
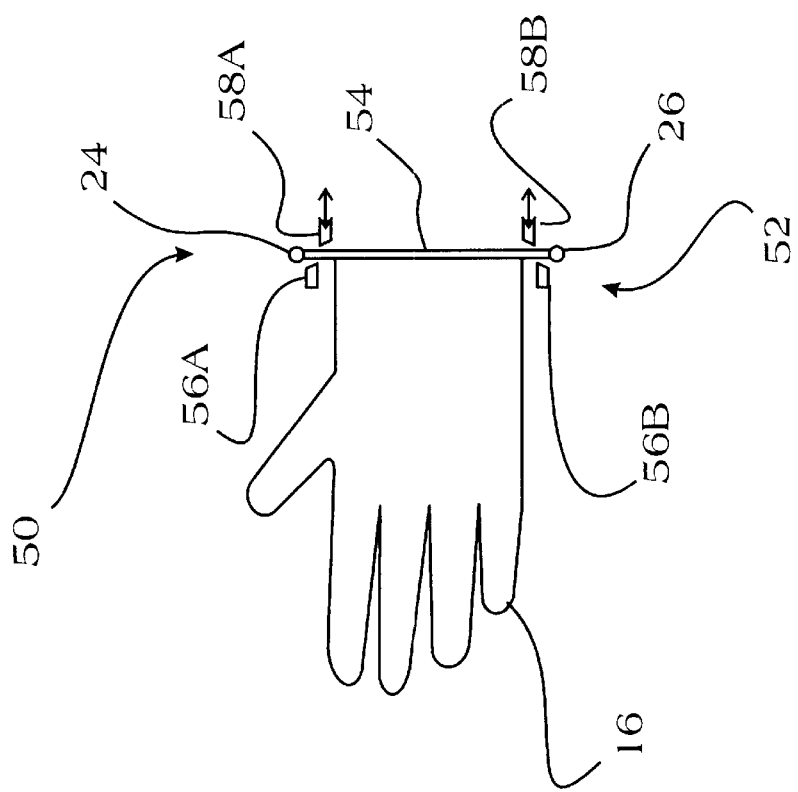
FIGURE 4B
FIGURE 4A

GLOVE DISPENSER

This application is a continuation of application Ser. No. 09/531,395, filed Mar. 21, 2000, now pending.

BACKGROUND OF THE INVENTION

1. Field of the Invention

This invention relates generally to disposable sanitary gloves and, more specifically, to an Improved Glove Dispenser.

2. Description of Related Art

Individuals in the health care industry regularly don disposable sterilized gloves in order to prevent the transmission of bacteria or other contaminants to themselves and to others. It is typical for these gloves to be dispensed from a common cardboard box similar to those used to dispense disposable facial tissues. In order to don a pair of gloves, the individual typically grabs a glove and pulls it from the box using an uncovered hand. Using one ungloved hand, the user slips the glove on to the other hand, after which the gloved hand is used to grab the second glove from the box and then to don it upon the ungloved hand. If we analyze the steps in this process, we can see that while the gloves originally started out being clean and antiseptic, by the time they are actually on the user's hand, they are likely to be anything but clean. In particular, the current (widely used) method requires the first glove and the glove dispenser to be touched by ungloved hands. As such, the first glove donned can no longer be expected to be sanitary. Furthermore, the user then uses this potentially soiled glove to grab the second glove in order to don it. It is not a stretch to believe that both gloves are no longer sterile and clean. In particular, it has been reported by the Centers for Disease Control and Prevention that an estimated 260,000 patients a year actually acquire a staff infection while they are in a hospital (that they didn't have before entering the hospital). This amounts to approximately 13% of all the infections acquired within hospitals. These staff infections in particular are believed to be transmitted easily between the faces and the hands of human beings, and as such, would be easily transmitted in the aforementioned glove-donning process.

What is needed is a system that permits a user to don sanitary gloves without the need for them to first touch the outside of these gloves. In this way, the gloves would remain sanitary, even through the donning process.

SUMMARY OF THE INVENTION

In light of the aforementioned problems associated with the prior devices, it is an object of the present invention to provide an Improved Glove Dispenser. It is an object that the device of the present invention permit a user to don gloves without first touching their exterior. It is a further object that the device include a plurality of gloves attached by their cuffs to a filament, with the filament and cuffs being dispensed from an exchangeable glove cartridge. It is yet another object that the dispenser be responsive to a user's voice. It is still another object that the invention provide a new method for donning gloves that will prevent user contamination of the gloves by touching the exterior of the gloves during the donning process.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

FIGS. 4A and 4B are partial cutaway side views of the dispensing mechanism of FIG. 3.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide an Improved Glove Dispenser.

Figure 1:
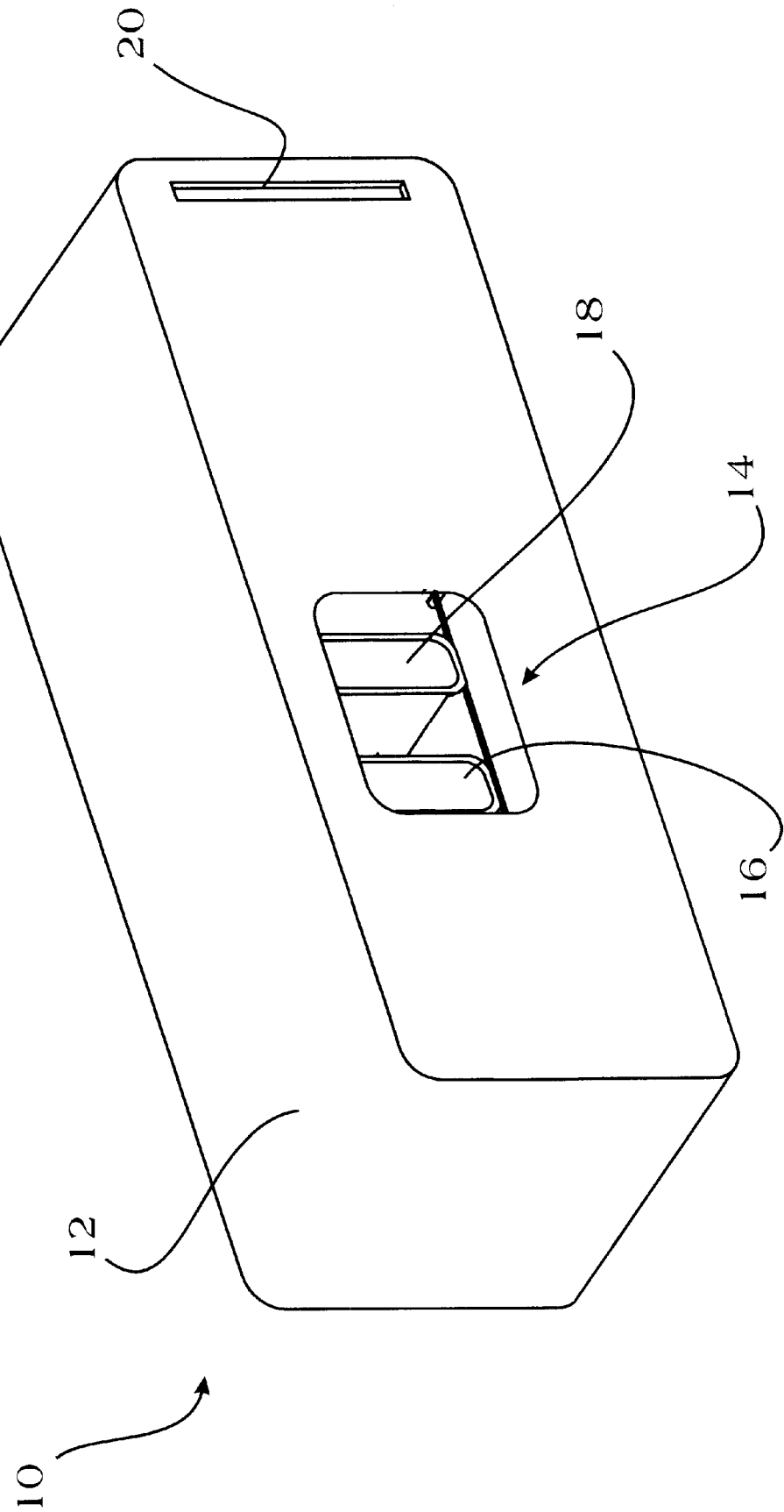
FIG. 1 is a perspective view of the improved glove dispenser of the present invention.

The present invention can best be understood by initial consideration of FIG. 1. FIG. 1 is a perspective view of the improved glove dispenser 10 of the present invention. While a variety of different shapes and configurations might be provided, the one depicted is a preferred configuration. As can be seen, the dispenser 10 comprises a housing 12 which includes a window 14 formed within it into which a user may insert his or her hands into a pair of gloves 16 and 18. As can be seen, the cuffs of the gloves 16 and 18 are held open such that the user need not touch the outer surface of the gloves 16 and 18 prior to donning them. Once the user's hands are fully inserted into the gloves 16 and 18, these gloves are cut free and the user can resume his or her tasks. A variety of other features may be provided on the housing 12, including an aperture 20, which will be discussed more fully below in connection with other figures. If we now turn to FIG. 2, we can examine exactly how the preferred system works.

Figure 2:
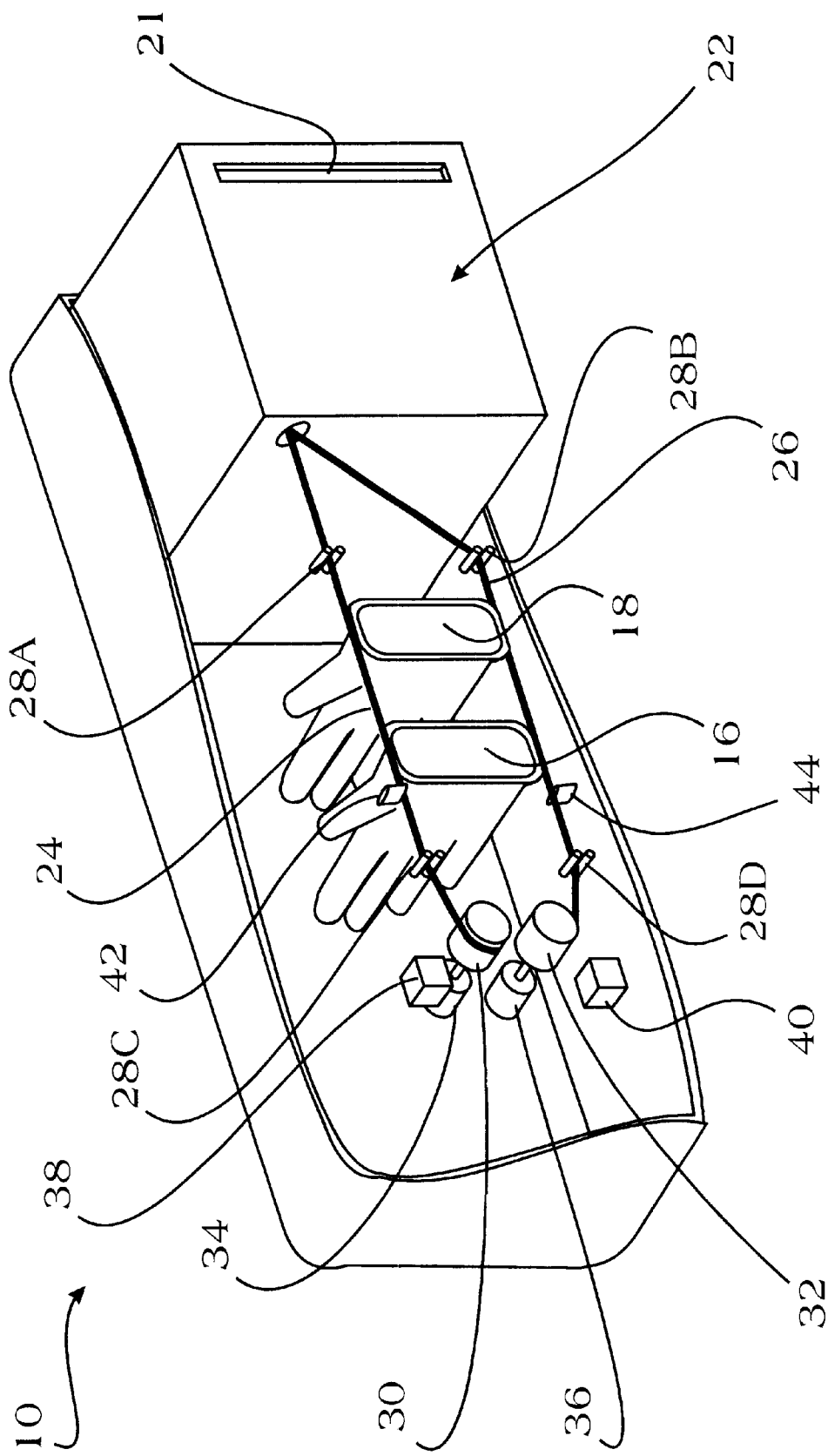
FIG. 2 is a partial cutaway perspective view of the dispenser of FIG. 1.

FIG. 2 is a partial cutaway perspective view of the dispenser 10 of FIG. 1. As can be seen in FIG. 2, the dispenser 10 preferably includes a replaceable glove cartridge 22 from which a first filament 24 and a second filament 26 are dispensed. After exiting the cartridge 22, the filaments 24 and 26 preferably pass through respective guide means 28A and 28B. These guide means are preferably a pair of rollers in this embodiment, but it should be understood that a first and second feed paths 25 and 27, respectively, may comprise the guide means 28 described herein, or they may comprise some other arrangement, including a simple track design.

After entering the feed paths 25 and 27, the filaments 24 and 26 then pass in front of the window 14 and then through two more guide means 28C and 28D, after which the filaments 24 and 26 are coiled around first and second drive wheels 30 and 32. As can be seen, the filaments 24 and 26 have gloves 16 and 18 attached between them, such that when the guide means 28 spread, the two filaments 24 and 26 (and therefore the gloves 16 and 18) are stretched in order to provide a wide opening into which the user can insert his or her hands. Once the user has inserted the hands into them, the gloves 16 and 18 will be cut free from the filaments 24 and 26 by an apparatus disclosed below. Once the gloves have been cut free, the filaments 24 and 26 can advance through the second set of guide means 28C and 28D where they are taken up around the first and second drive wheels 30 and 32.

The drive wheels 30 and 32 are preferably driven by first and second motors 34 and 36, respectively. The motors 34 and 36 are controlled by first and second control means 38 and 40. The control means 38 and 40 are responsive to a variety of inputs. They essentially dictate to the motors 34 and 36 when the filaments 24 and 26 should be advanced. For example, the control means 38 and 40 may be responsive to a foot pedal, a push-button, and they may further be responsive to a voice command, after which the control means 38 and 40 will command the respective motors 34 and 36 to advance the drive wheels 30 and 32, such that a fresh pair of gloves is stretched open for donning.

It may further be desirable to include first and second detector means 42 and 44 that are situated to detect when a glove has reached its donning location within the window, at which time the motors 34 and 36 will be commanded to stop. By providing two separate detector means, the first and second filaments 24 and 26 can be advanced independently until the gloves 16 and 18 are in exactly the right position and to account for any filament stretching or differences in the guide path for the filaments 24 and 26.

As a final attribute, we can see that the cartridge 22 includes an aperture 21 formed within it through which the height of the unused glove level can be observed. The aperture 21 is preferably aligned with the aperture in the housing (see FIG. 1) such that a user can visually check the amount of unused gloves left in the cartridge 22. If we now turn to FIG. 3, we can further examine the improvement of this present invention.

Figure 3:
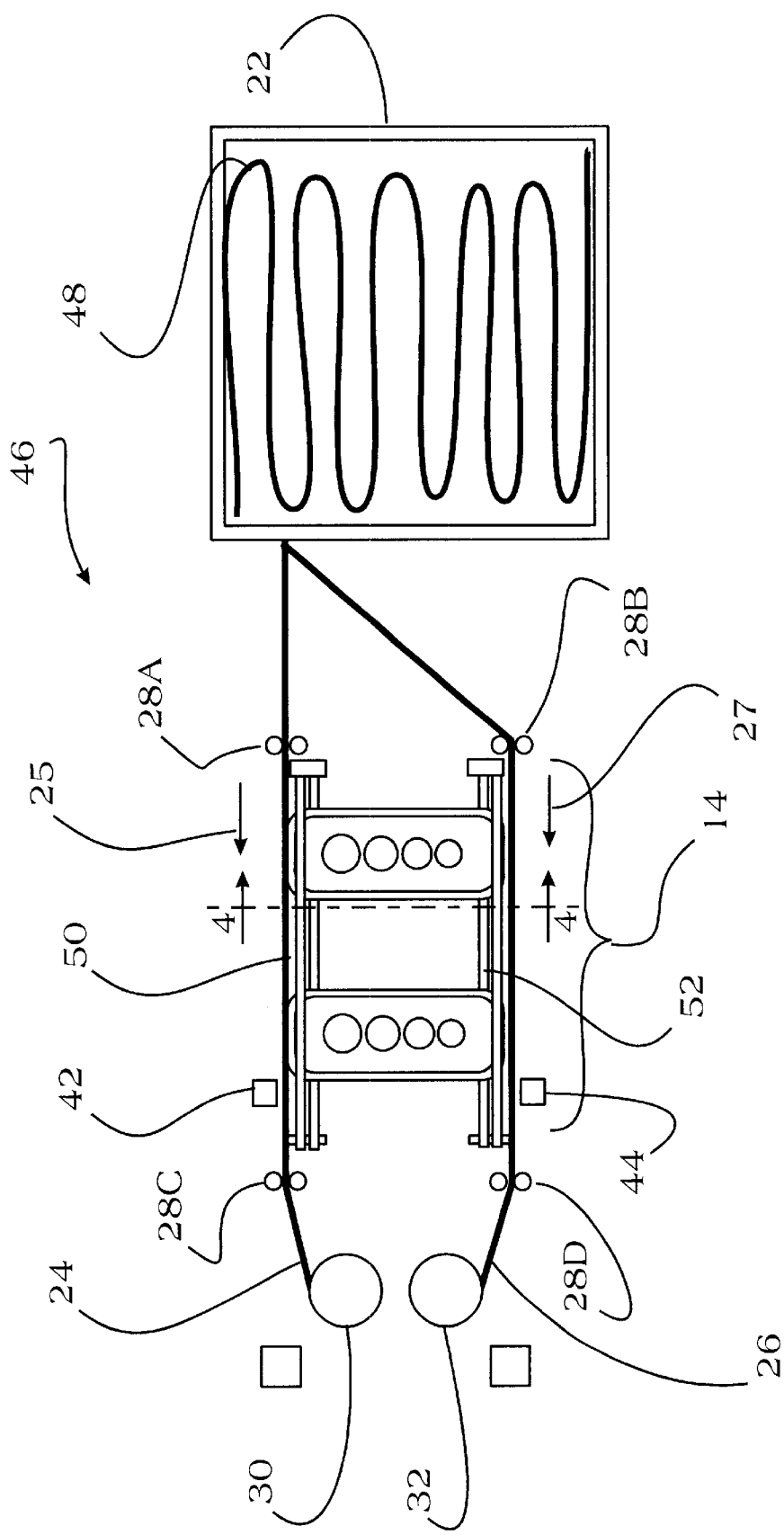
FIG. 3 is a front view of the dispensing mechanism of the dispenser of FIGS. 1 and 2.

FIG. 3 is a front view of the dispensing mechanism 46 of the dispenser 10 of FIGS. 1 and 2. As can be seen in FIG. 3, within the cartridge 22 is a stack of gloves 48. These gloves are essentially laid back and forth on top of one another such that when the filaments 24 and 26 are pulled, the gloves are dispensed out through the side of the cartridge 22. The filaments 24 and 26 then pass through the guide means where the gloves 16 and 18 are stretched open for donning. Once the hands are within the gloves, they are cut free from the filaments 24 and 26 by command of the user. In its preferred form, the gloves 16 and 18 are cut free by first and second shears 50 and 52. These preferably mechanized shears 50 and 52 will cleanly cut gloves 16 and 18 from the filaments 24 and 26, after which the drive wheels 30 and 32 can advance the filaments 24 and 26 until the next pair of gloves is stretched and ready for donning. When the last set of gloves has been dispensed and the cartridge is empty, it is a simple matter of exchanging the expended cartridge 22 with a fresh cartridge. Each fresh cartridge 22 should be provided with a pair of lengths of bare filament (as leaders) to permit the user to thread the filaments through the guide means 28 and around the drive wheels 30 and 32. The system is then closed up and the drive wheels 30 and 32 advance the filaments until such time as a glove is detected by first and second detector means 42 and 44 which indicates that the gloves are in the donning position.

FIGS. 4A and 4B are partial cutaway side views of the dispensing mechanism 46 of FIG. 3. As can be seen in FIG. 4A, the glove 16 further comprises a cuff 54. The cuff is typically a reinforced area of the glove 16 to give it additional strength where it wraps around the user's wrist and further to prevent rolling when the user is inserting their hand into the glove 16. As can be seen, the cuff 54 is stretched between the first and second filaments 24 and 26 at the point of donning. As can further be seen, the shears 50 and 52 preferably comprise a pair of inner blades 56A and 56B and a pair of moving outer blades 58A and 58B. As can be seen, the outer blades 58 are designed to be movable towards the inner blades 56, thereby cutting the cuff 54 free from the filaments 24 and 26.

The shears 50 and 52 are preferably motor or otherwise mechanically-operated to provide hands-free operation to the user. As can be seen, once the cuff 54 is cut free, the user can simply pull his or her (now gloved) hands out of the dispenser thereby permitting the filaments 24 and 26 to advance and expose a fresh set of gloves. It should be noted that the gloves are not specifically right- or left-handed, and as such, gives the user the flexibility to only don a glove on a single hand without disturbing the glove queue.

FIG. 4B depicts an alternative embodiment of the shears. As can be seen in FIG. 4B, the guide means comprises a pair of channels 60 and 64. These channels 60 and 64 provide a path through which the filaments 24 and 26 are spread apart and thereby stretch the cuffs 54 of the glove 16. In this case, the alternative outer blades 59A and 59B have to cut the cuff 54 free from the filaments 24 and 26 by crimping the cuff 54 against the edge of the channels 60 and 64. Since the material of the gloves is thin, it should not require much force to cut through the cuff 54. It should be understood that these are simply two examples of preferred shears. Other embodiments might include manual shears and/or shears that cut through application of heat to the cuff 54. If we finally turn to FIG. 5, we can examine yet another preferred embodiment of the present invention.

Figure 5:
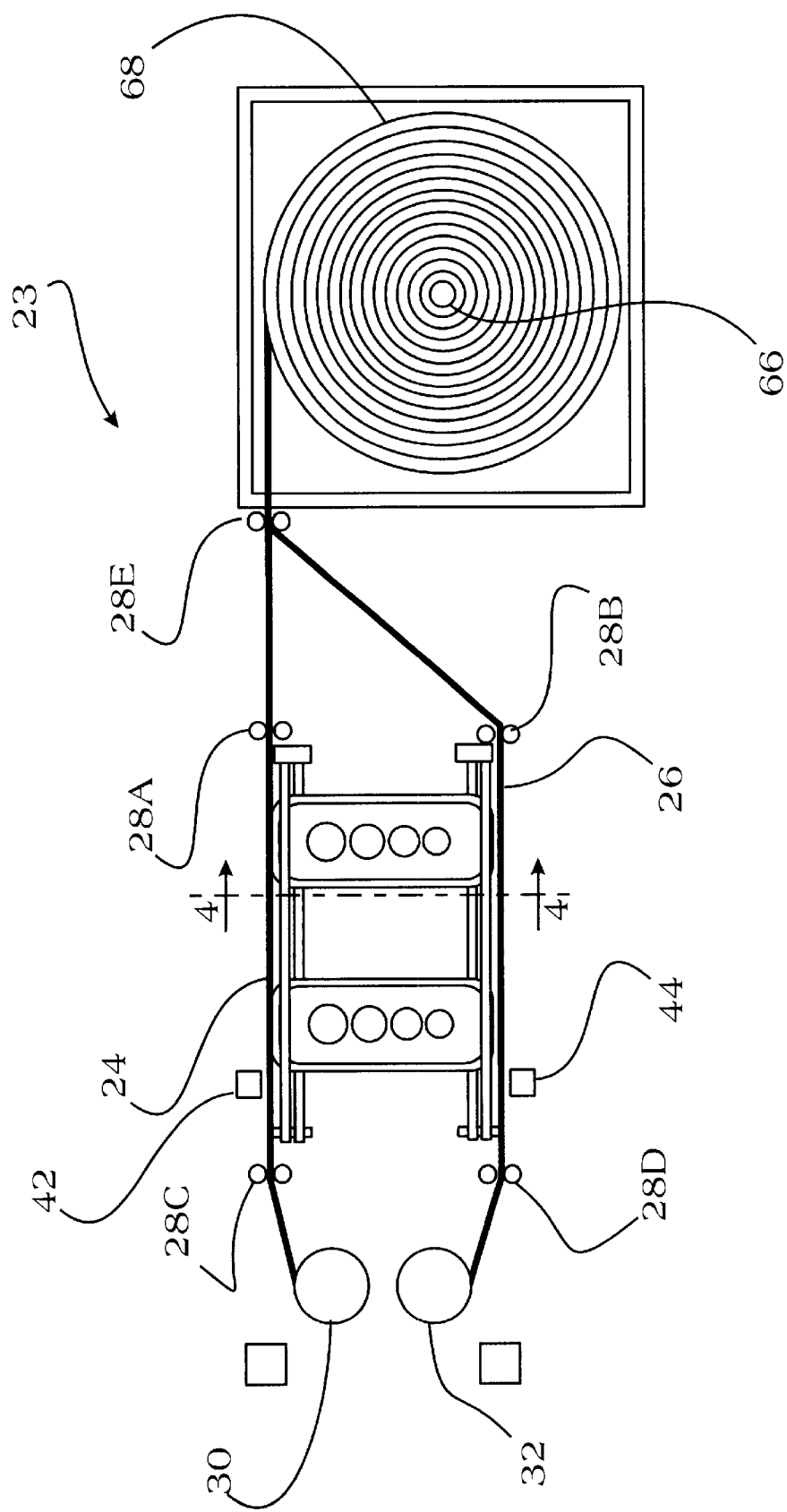
FIG. 5 is a partial cutaway front view of an alternative glove cartridge of the dispenser of FIGS. 1 through 4.

FIG. 5 is a partial cutaway front view of an alternative glove cartridge 23 of the dispenser 10 of FIGS. 1 through 4. As can be seen, the alternative cartridge 23 comprises a shaft 66 around which a string of filaments and gloves are wrapped to form a glove reel 68. The glove reel 68 is dispensable through guide means 28E, after which the filaments 24 and 26 separate and pass through another set of guide means 28A and 28B. The benefit of this alternative glove cartridge 23 is that the glove reel 68 can be wrapped fairly tightly and may provide improved control of the dispensing of the gloves. Furthermore, the shaft 66 may be used to create tension on the filaments 24 and 26 to ensure that they are stretched tightly apart at the donning station.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An improved dispenser for gloves, comprising:
    glove stock, comprising a pair of filaments between which a plurality of disposable gloves are attached in spaced arrangement;
    first guide means for guiding one said filament through a first feed path;
    second guide means for guiding the other said filament through a second feed path; and
    shears for separating said gloves from said filaments.

2. The dispenser of claim 1, wherein said gloves are defined by a cuff, a thumb side and a bottom side, said gloves being attached to one said filament at said thumb side of said cuff and to the other said filament at said bottom side of said cuff.

3. The dispenser of claim 2, further comprising a donning window, whereat said first feed path is separated from said second feed path by a distance sufficient to open said cuffs of said gloves an amount adequate to permit a user to insert their hand through said cuff.

4. The dispenser of claim 3, wherein shears comprises first shears and second shears, said first shears being located adjacent to said first feed path in said donning window and said second shears being located adjacent to said second feed path in said donning window.

5. The dispenser of claim 4, further comprising housing means for containing said dispenser, and wherein said glove stock is contained within an exchangeable glove cartridge.

6. The dispenser of claim 5, further comprising first and second drive wheels, said first drive wheel being rotatable by first motor means in response to first control means, and said second drive wheel being rotatable by second motor means in response to second control means.

7. The dispenser of claim 6, wherein said first and second control means are responsive to glove location along said first and second feed paths.

8. The dispenser of claim 7, wherein said first and second control means are responsive to user input.

9. The dispenser of claim 8, wherein said first and second control means are responsive to a user's voice.

10. The dispenser of claim 7, further comprising first and second limit switch means for detecting the location of said gloves along said feed path, said first control means being responsive to said first limit switch means and said second control means being responsive to said second limit switch means.

11. The dispenser of claim 4, wherein each said shears comprises an inner blade and an outer blade, said inner and outer blades cooperating to cut said glove free from one said filament.

12. A glove dispensing process, comprising the steps of:

advancing first and second filaments of glove stock through first and second feed paths, said glove stock further comprising a plurality of gloves defined by cuffs attached by said cuffs in spaced arrangement along said filaments; cutting a glove free from said filaments.

13. The dispensing process of claim 12, further comprising a stopping step between said advancing and said cutting steps, said stopping step being responsive to said glove position along said feed paths.

14. The dispensing process of claim 13, wherein said advancing is responsive to user input.

15. The dispensing process of claim 14, wherein said advancing is responsive to a user's voice.

16. The dispensing process of claim 14, wherein said advancing is responsive to a foot-activated pedal.

17. The dispensing process of claim 12, further comprising a loading step prior to said advancing step, said loading step comprising loading a glove stack into a dispenser device.

* * * * *